United States Patent [19]

Gudmundsson

[11] Patent Number: 5,536,893

[45] Date of Patent: Jul. 16, 1996

[54] METHOD FOR PRODUCTION OF GAS HYDRATES FOR TRANSPORTATION AND STORAGE

[76] Inventor: Jon S. Gudmundsson, Alfheimsvingen 4, N-7026 Trondheim, Norway

[21] Appl. No.: 195,748

[22] Filed: Jan. 7, 1994

Related U.S. Application Data

[63] Continuation of PCT/NO91/00101, Jul. 8, 1991, now abandoned.

[51] Int. Cl.$^6$ .................................................. C07C 7/20
[52] U.S. Cl. ........................... 585/15; 62/45.1; 208/187
[58] Field of Search ............................. 585/15; 95/153; 208/187; 62/45.1

[56] References Cited

U.S. PATENT DOCUMENTS

| | | | |
|---|---|---|---|
| 3,514,274 | 5/1970 | Cahn et al. | 48/190 |
| 3,888,434 | 6/1975 | Chersky et al. | 243/38 |
| 3,975,167 | 8/1976 | Nierman | 48/190 |
| 4,915,176 | 4/1990 | Sugier et al. | 166/371 |
| 4,920,752 | 5/1990 | Ehrsam | 62/46.1 |

Primary Examiner—Asok Pal
Assistant Examiner—Bekir L. Yildirim
Attorney, Agent, or Firm—Dennison, Meserole, Pollack & Scheiner

[57] ABSTRACT

Method for the production of gas hydrates for storage and transportation of hydrate forming gases. The gas is pressurized and cooled, whereupon the gas (1b) is supplied to a vessel (6), to which water (7) is added simultaneously to the vessel (6) to form fine water droplets that are dispersed in the gas (1b) supplied. The temperature and pressure in the vessel (6) are adjusted to produce hydrate from water and gas. The gas (1b) supplied and the water droplets (7) react to form hydrate (8a); then the hydrate is then withdrawn from the reactor (6), optionally cooled in a cooling apparatus (11), and then passed to an agglomeration step (12) to agglomerate the hydrate (8a), thus increasing the density of the hydrate (8a) and to embed more gas in the interstices between the hydrate particles (8a). The agglomerated hydrate particles (8a) are transported to a suitable transportation unit or storage container to transport/store the hydrate at adiabatic conditions at atmosphere pressure or at a slight gauge pressure at a temperature below 0° C., preferably at minus 10° C. to minus 15° C.

20 Claims, 7 Drawing Sheets

METHOD FOR PRODUCTION OF GAS HYDRATES FOR TRANSPORTATION AND STORAGE

This application is a continuation of International Application PCT/NO91/00101 designating the United States, now abandoned.

The present invention concerns a method as stated in the introductory of patent claim 1, for the production of gas hydrates stable for storage, particularly hydrates of natural gas or associated natural gas, for onshore and offshore transportation or for the storage of the same.

BACKGROUND

In cases where a pipe system for transporting gas, either natural gas or gas mixed with other hydrocarbons is unavailable, it is difficult to carry out an efficient use. In such cases, continious combustion of the gas is impossible, it cannot be used on the spot, e.g. at an offshore platform, or transported to the customer through a pipeline.

One possibility in such situations is to re-inject the gas to the reservoir to promote the oil production. The development of certain isolated gas fields, e.g. offshore, is economically impossible without permitting utilization on the spot or transportation through a pipeline.

It is also possible to carry out treatment on the spot by producing liquidous natural gas, methanol and ammonia. However, these three possibilities require extensive treatment of the natural gas and/or another gaseous product and requires equipment that is comprehensive and on a scale that is not suited for offshore production.

U.S. Pat. No. 3,514,274 discloses a method for solving the transportation problem, in which natural gas is converted to hydrates and transported/stored in propane or other $C_4$–$C_5$ hydrocarbons. In this case, the propane is used as a recyclable energy carrier, and the natural gas hydrate is dehydrated at the delivery point and convened to pure natural gas simultaneously with converting the propane to propane hydrate. Then, the propane hydrate can be used again for the production of natural gas hydrate, in which compressed and cooled natural gas is contacted with propane hydrate in a reactor, thus converting propane hydrate to propane carrier liquid and natural gas to natural gas hydrate. However, this method has the disadvantage that dead weight, i.e. propane, must be transported all the time. Moreover, the transportation and storage temperature must be as low as −22° C. to avoid evaporation of the propane carrier liquid.

NO 149976, patent publication laid open to public inspection, discloses a method for transporting natural gas in a boat submerged in water. Natural gas and fresh water is separately fed into a submerged marine ship and combined to form gas hydrate, whereupon the hydrate is kept stable during transportation by means of the hydrostatic pressure and the relatively low temperature of the sea water. However, this method requires that the pressure and the temperature is maintained throughout transportation, and requires use of specially contructed submarines that have a low loading capacity compared with surface ships. Moreover, problems may arise if the shipping terminals are located in an area with shallow and relatively warm water. Moreover, the method disclosed in this patent publication is naturally limited to marine transportation only, and will not contribute to a solution where only pipeline transportation or transportation as LNG is available.

In other cases, one faces gas emission such as polluting by-products from industrial processes where a removal of the gas is desired but purification or destrucion on the spot is impossible.

OBJECT

The main object of the present invention is to provide a method for the treatment of hydrate forming gases, such as natural gas or natural gas mixed with or enclosed in other hydrocarbons or water, or polluting gases or gas to be supplied to an industrial or biotechnical process that permits economically satisfactory storage, transportation and use of the gas without using pipeline or immediate transportation by tankers or tank cars, and without the need for use of pressure or any carrier liquid during transportation or storage.

Another object of the invention is to provide a method that in addition is environmentally acceptable and that can be realized with an acceptable risk with respect to security and economy.

BRIEF DESCRIPTION OF THE INVENTION

The principle of the invention is stated in the characterizing part of patent claim 1. Further beneficial features of the invention are stated in the remaining patent claims.

The present invention concerns a method for the production of storage stable gas hydrates from water and hydrate forming gases, such as $CO_2$, $H_2S$, natural gas and associated natural gas, just to mention a few. However, in the following, natural gas is in general described as the gaseous component in the production process, but it should be evident that a person skilled in the art can apply the principle of the invention to consider hydrate forming gases other than natural gas, and the invention should for that reason not be regarded as limited to use of natural gas only. The present method for production of gas hydrates can be adapted to both onshore and offshore operation.

At the production site, oil and water is separated from the natural gas and natural gas mixed with other hydrocarbons, whereupon the purified gas is compressed and cooled. The condensed gas produced by this compression and cooling is removed in a separator, in which temperature and pressure is adjusted to produce predetermined hydrocarbons, preferably butane and higher hydrocarbons. The separated cooled gas is further compressed and passed through a heat exhanger and cooled.

The compressed gas is then guided to a reactor vessel and, together with pressurized water, expanded to a lower pressure through nozzles or the like, thus producing fine droplets disperged in the expanded natural gas. The water and the gas will react almost immediately to produce natural gas hydrate comprising frozen water with enclosed gas. The pressure and temperature conditions in the reactor are adjusted to favor hydrate formation, and the gas pressure prior to expansion is preferably adjusted to provide cooling during expansion by means of the Joule-Thomson effect. Provided that there is a defined ratio between pressure and temperature that represents equilibrium between gas hydrate and water, the reactor temperature is preferably decreased a few degrees below the equilibrium temperature, thus increasing the reaction rate for the formation of natural gas hydrate. A sub-cooling from 1° to 10° C. is in most cases sufficient, and a typical sub-cooling varies from 2° to 6° C.

The natural gas hydrate, formed as fine powder, is transported out of the reactor either by the reactor gauge pressure or by means of a mechanical transportation apparatus. Any excess gas is then separated from the hydrate powder, e.g. in a cyclone, whereupon the separated gas is compressed, cooled and recirculated back to the hydrate reactor. The hydrate powder is then cooled partly by ordinary heat loss during flow in the transportation pipe and partly through expansion to a lower pressure and optionally further cooling in a heat exchanger. The cooled hydrate powder is then optionally transferred to an agglomeration step, such as pressing or pelletizing, to provide a more dense natural gas hydrate and to embed further gas in pores. The resulting hydrate particles can then optionally be provided with a protective ice shell by spraying them with water, whereupon the water will freeze and form ice. In cases where the hydrate particles are unable to provide proper cooling to the water droplets added, further cooling must be provided, e.g. by cooled gas flowing through the wetted hydrate particles. The ice shell will provide more fracture strength and thermal insulation. If desired, the ice shell can also be strengthened with reinforcing materials, such as fibers, to further strengthen the ice shell and therefore the hydrate particles.

The hydrate particles are then cooled to a suitable storage temperature, and the particles can be stored or transported stable for a longer time, up to several weeks, at adiabatic conditions and at a pressure near atmospheric pressure. At a later stage when the gas is to be used, heat is supplied to the natural gas hydrate to decompose same to form gas and ice. The water can, if desired, be recycled or discharged, without any environmetal risks. However, it is an advantage to recycle the water back to the gas hydrate production process, firstly because the water itself represents a low temperature reservoir, and secondly because the water, provided that it is kept at a temperature below +30° C., still contains seeds that promotes the reaction rate for the hydrate formation, as further described below.

TRANSPORTATION AND STORAGE

The gaseous hydrate particles can be used for storage and transportation of gases. They can also be used for operating transporting means onshore and offshore. Other gases may also be used to produce the gaseous hydrate particles. These other gases can be commercial products or pollutants or other gas types that form in natural or industrial processes. Gaseous hydrate particles can be used in power stations and in processes intended for reduction of pollution. Gaseous hydrate particles can be used where gas has to be added in large mounts, in aquatic enviroments, both natural and artificial.

The gaseous particles can be stored in offshore platforms in subsea vessels under pressure. These vessels can be located on the sea bed or adjacent to the platform. They can be pressurized hydrostatically with a water column through a valve arrangement with manometer to keep the vessel and the sea water separated by means of a water column. The gaseous particles can be stored as solid material in gas or surrounded by cooled water or a hydrocarbon based liquid. In addition to subsea vessels, tankers, barges and the like can be used, or submerged vessels made up of a stiff or flexible material.

Hydrate particles with embedded gas can be transported from offshore storage vessels by boat, tankers, barges or floating containers towed by tugboats to the shore. In the most preferred arrangement, hydrate particles are pumped from the storage vessels offshore through a pipeline to a tanker. The tanker can, but does not need to, be able to store the particles under gauge pressure. The particles can be transported to the shore as solid cargo or in water or in a hydrocarbon based liquid. Gas that escapes from the particles during transportation can be pressurized and/or used to operate the tanker and the cooling equipment.

Hydrate particles can also be stored in underground storage rooms, such as large caverns blown in rock formations. This can be accomplished by cooling/refrigerating the underground storage cavern prior to the supply of gas hydrates, so that any naturally occuring water freezes and forms an isolating ice shell on the "vessel" walls. In this way, gas escape from the storage cavern can be prevented. Like ordinary isolated vessels, the gas hydrate produced in accordance with the invention can be stored near atmospheric pressure, as descirbed in further detail below.

The hydrate particles with embedded gas are after the transportation pumped or transferred by other ways from the tanker to one or several storage tanks onshore. The particles melts and the gas can escape. The melting can be accomplished using different types of heating, e.g. with emission from a gas operated power station. Cold melting water can be used as coolant for any power station, thus making the ordinary cooling towers redundant.

When the tanker is emptied, melting water and process water can be loaded. The water can have its origin from a former cargo. The melting water will be ballast for the tanker from the shore to an offshore platform. When the tanker loads the particles at the platform, the melting water is unloaded. The vessels at the platform accept the melting water for use in the hydrate production. If desired, air may be removed from the melting water and the process water and optionally pre-treated. The air removal can be effected onshore and/or offshore. In addition, the water can be used for injection to a reservoir.

Transferring hydrate particles from e.g. the production unit to a storage vessel or transportation vessel can be accomplished by using pneumatic transportation systems. The carrier gas is in this case peferably cooled natural gas as opposed to air that is used in ordinary pneumatic transport systems. The use of cooled natural gas in such systems will cool the hydrate particles during transportation and thus contribute in a positive manner to particle stability.

BRIEF DESCRIPTION OF THE DRAWINGS

In the following, the invention is described in further detail with reference to the drawings, in which.

DETAILED DESCRIPTION OF THE DRAWINGS

Figure 1:
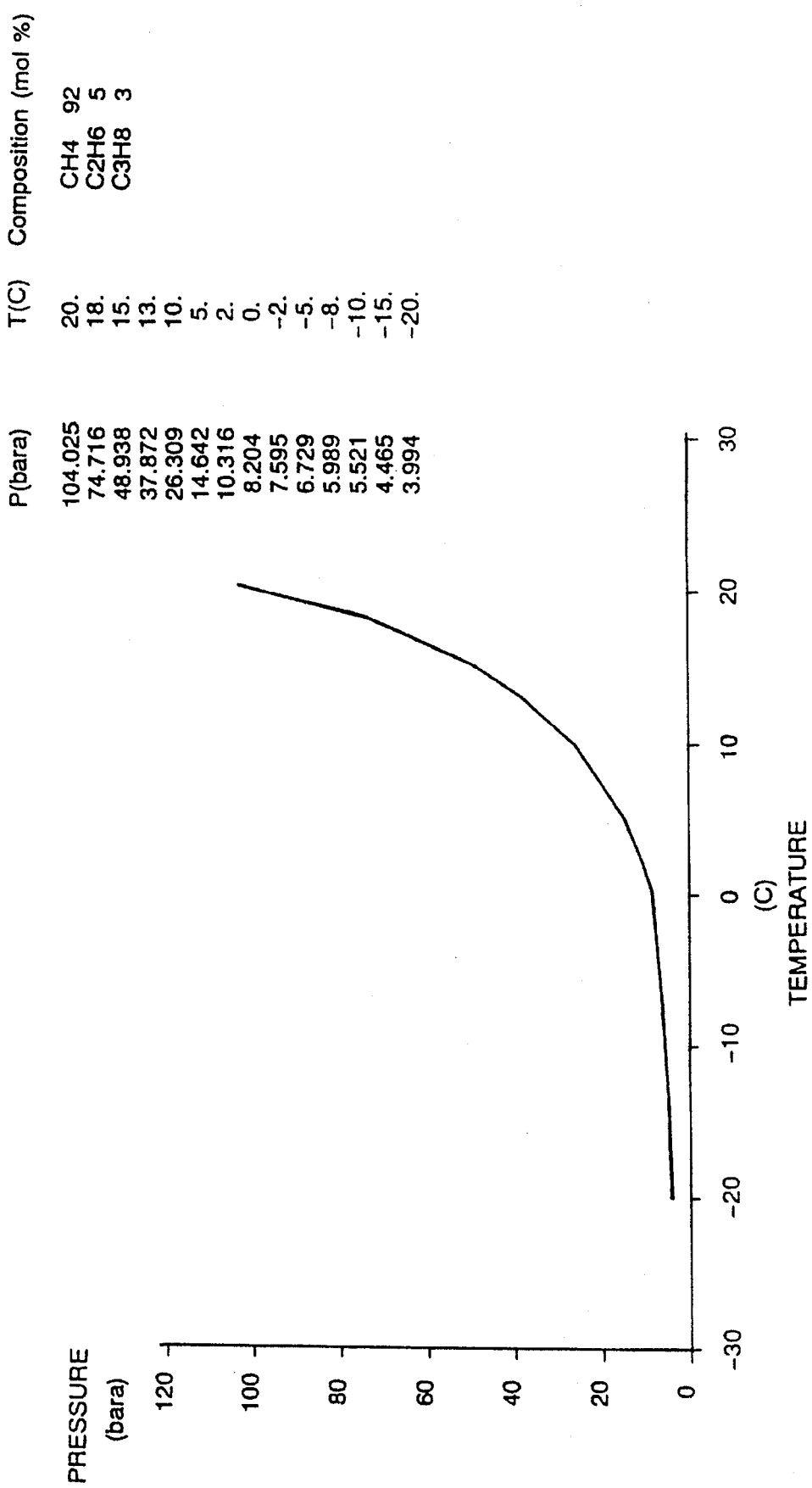
FIG. 1 is a hydrate equilibrium diagram for a typical treated natural gas for use with the present invention.

FIG. 1 shows a pressure/temperature diagram for a typical treated natural gas, applied as an example in the method in accordance with the present invention, the diagram provided with a equilibrium curve for hydrate. The gas in the example comprises, after the removal of heavier hydrocarbons, 92% methane, 5% ethane and the remainder propane. However, the treated gas can nevertheless contain small amounts of other gases, such as carbondioxide, oxygen or air, without adversely effecting the subsequent production of hydrates. As appears from the curve, it is not necessary that the formation temperature for hydrate be lower than 0° C. According to FIG. 1, the formation pressure for natural gas hydrate is 104 bar at +20° C., whereas the formation pressure at 0° C. will be about 8 bar. Hydrate formation will occur at the high pressure side/low temperature side of this curve. Water can establish two different lattice types, the first having an empiric formula of $8X \cdot 46H_2O$ (where X represents one gas molecule) and the second $24X \cdot 136 H_2O$, provided that all cavities in the crystal lattice are occupied by gas. These crystals form a lattice having relatively large cavities that are occupied by gas. Accordingly, the gas is not directly bonded to the water molecules in the crystal, but is merely captured by the crystal's geometric limitations until the lattice structure breaks down. The heat of formation for gas hydrate is exothermic and, to keep the temperature in the reactor system constant, the reaction heat must be removed from same, partly by means of gas expansion cooling and partly by means of indirect or direct cooling of the reactor.

In theory, gas hydrates are unstable at atmospheric pressure, and even at −15° C. a pressure of e.g. at least 4.5 bar is required to keep the hydrate exemplified in FIG. 1 in a stable state. To disintegrate a hydrate into its respective components, it is required to supply the hydrate with its dissociation heat, and will accordingly assume a meta stable state at adiabatic conditions in a cooled state, even at pressures close to atmospheric pressure. Experiments carried out in connection with the present invention have demonstrated that natural gas hydrate is stable even at an ambient temperature of −1.5° C. The bulk mass of hydrate will serve as isolation itself and only hydrate particles located close to the vessel walls will recieve heat from the surroundings. In this way, bulk cargo of hydrate can be transported/stored in a stable state, provided that the vessel is thermally insulated with respect to the surroundings and that the temperature is kept at a low level. This meta stable state can be further improved by compressing the hydrate particles and optionally providing them with an external protecting ice shell.

Figure 2:
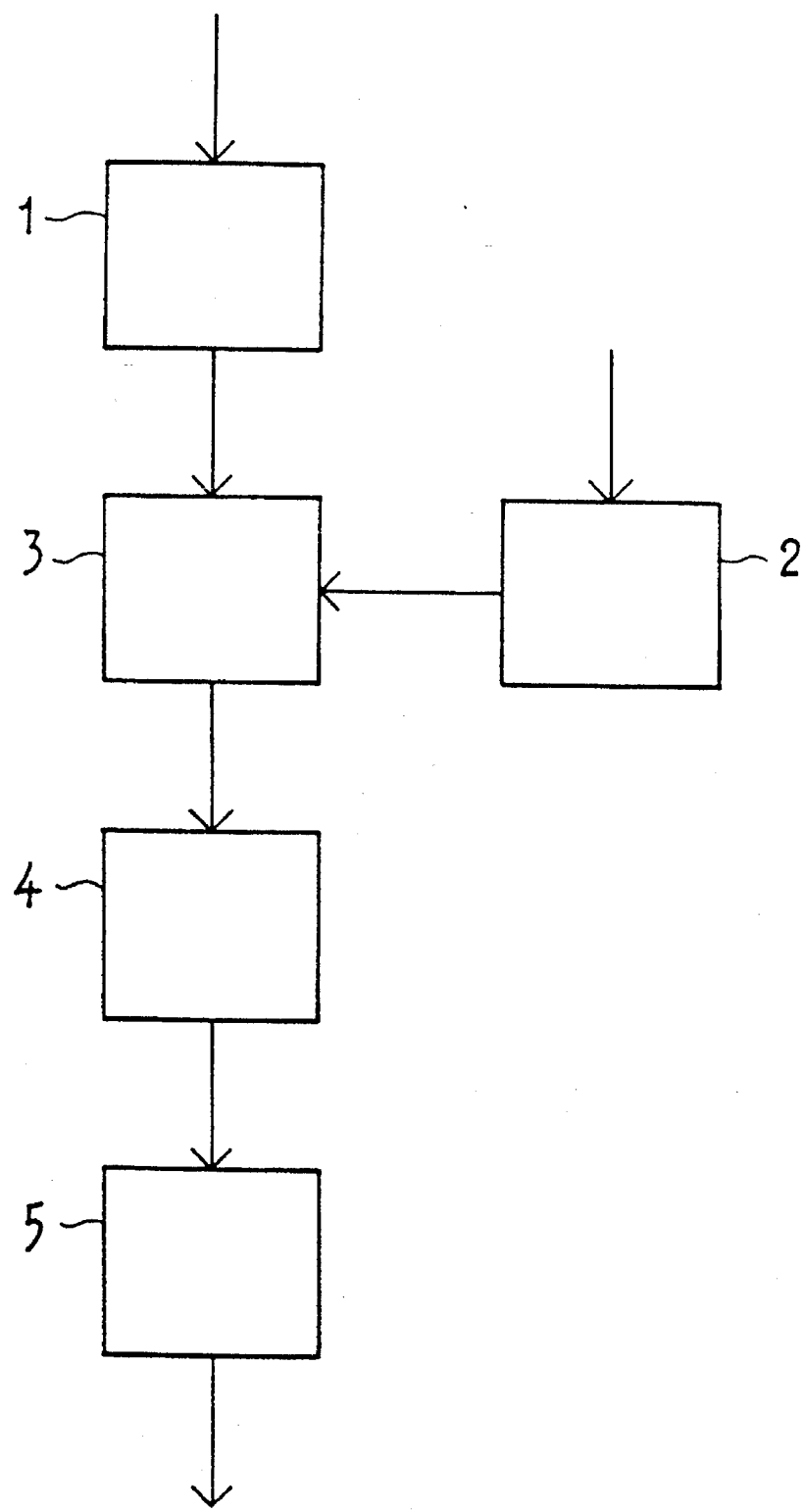
FIG. 2 is a simple diagram illustrating a general method for production of hydrates in accordance with the invention.

FIG. 2 illustrates in general a method for production of storage stable gas hydrates in accordance with the present invention. In process step 1, gas is pre-treated, e.g. by removing heavier hydrocarbons from natural gas, and thereafter in process step 2 is supplied to a reactor 2 together with water pre-treated in process step 1. The gas and the water react in accordance with the equilibrium conditions in question for hydrate formation and forms gas hydrate, in most cases with a snow-like appearance. The formed gas hydrate is then transported to process step 2, in which any unreacted gas and water is removed from the formed hydrate particles, whereupon the hydrate particles optionally are compressed/agglomerated and provided with a protecting ice shell. The formed and optionally post-treated hydrate particles are then further transferred in process step 5 to a transportation or storage container, in which storage or transportation occurs at conditions close to adiabatic and at a pressure close to atmospheric. The hydrate can then be stored for a longer period of time or transported for long distances without the risk of the hydrate decomposes into its respective components.

Figure 3:
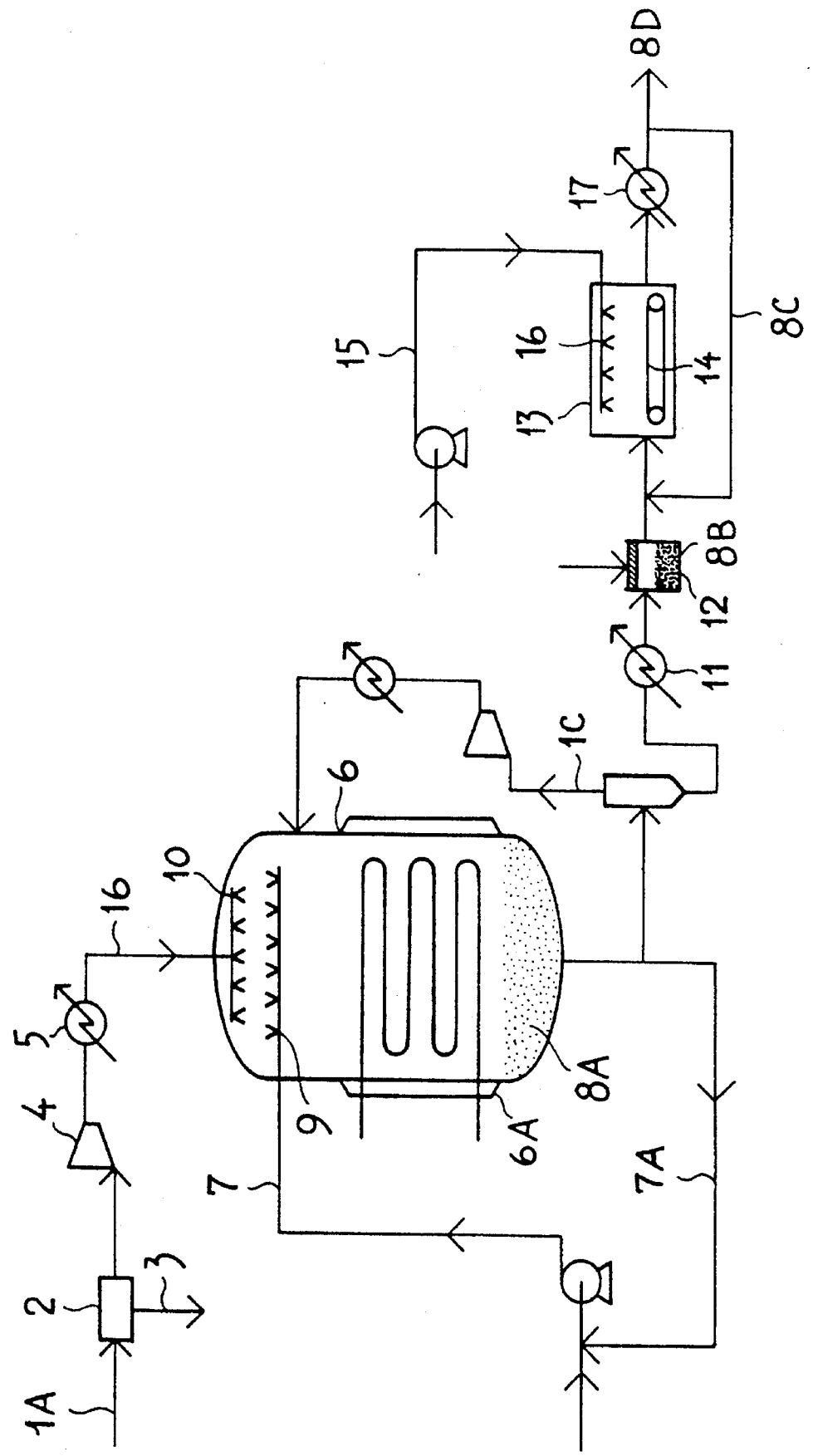
FIG. 3 is a simplified process flow sheet that illustrates the method for production of hydrate powder in accordance with the present invention.

In the following, a general method for production is presented with a discussion of the different aspects of this method with reference to FIG. 3.

Natural gas and natural gas mixed with other hydrocarbons is separated from oil and water (not shown) at the production site. The pruified gas is transferred through a compressor and cooled in a heat exhanger cooled by air or sea water. The condensed gas 1 produced from this compression and cooling step is removed in a separator 2; temperature and pressure is adjusted to produce predetermined hydrocarbons 3, preferably butane and higher hydrocarbons. These isolated liquidous components 3 can be used in combustion processes and in operation of platforms. The separated, cooled gas is compressed in a compressor 4 and passed through a heat exchanger 5 and cooled, e.g. by air or sea water.

The compressed and cooled gas is transported to a reactor vessel 6 that is also supplied with pressurized water 7, to produce gas hydrate 8a having embedded gas. This pressurized water 7 is supplied to the reactor through nozzles 9 or the like and expanded to a lower pressure and to a temperature that results in formation of gas hydrate 8a. The water pressure is not critical for the formation of gas hydrate, and the pressure can be adjusted to a desired level provided that the pressure is higher than the reactor pressure. However, the water pressure should be adjusted to achieve sufficient volumetric injection of water to the ractor and properly dispersing the water in the gas phase as fine droplets. Because of the exothermic character of the formation reaction, it is preferred that the construction and the operation conditions, particularly the pressure, is chosen to provide best possible cooling of the feed streams. This is accomplished by adjusting the pressure of the gas 1b supplied to the reactor vessel 6 to provide cooling by expansion (Joule-Thomson effect), and the expansion is in this case also carried out by means of nozzles 10. Moreover, it is favourable to adjust the reactor temperature a few degrees below the hydrate equilibrium temperature, generally 1°–10° C., preferably 2°–6° C., thus increasing the rate of hydrate formation. The formation rate can also be increased by adding small seeds of hydrate crystals to the water to be supplied to the reactor so that hydrate can more easily grow from these in the reactor. The formation of hydrate nucleus occur at the interface between the water and the gas bulk phase. The water 7 is perferably dispersed as thoroughly as possible in the gas bulk phase. The water can be supplied to the reactor 6 through the same openings, e.g. nozzles, as the gas, thus establishing a mixing effect at the supply location in the reactor. Moreover, water droplets in the reactor 6 can be dispersed in the gas bulk phase by, for example, means of a spreader means, such as a rotating plate with nozzles distributing fine droplets (preferably having a diameter if the order micrometer), or by using physical guiding or blocking means inside the reactor, or by using a stirrer (not shown). Recirculated unreacted gas can also be supplied to the reactor perpendicular to the main flow of fresh gas feed, thus achieving even better mixing of the reactants. However, the reactor pressure and the respective initial pressures for gas and water can be determined as desired, depending on the total pressure loss in the system and the gas pressure available. With respect to the process heat balance, a general rule says that the lower the reactor pressure, the less energy is required to produce gas hydrates based on the total energy content in the hydrate. On the other hand, the reaction rate for the formation of gas hydrate will increase with the pressure, and accordingly the reactor pressure must also be adjusted in view of the type of gas supplied to the reactor.

The gas hydrate formed in solid state (snow like appearance) is then transferred out from the reactor vessel, e.g. by means of a mechanical transportation apparatus or by means of the reactor gauge pressure. The hydrate particles 8a are separated from any unreacted gas, and liquidous water is removed. The pressure downstream of the reactor is controlled optionally by adjusting the operation pressure in the pipe connecting the reactor and the separator. For example, at an operation pressure of 50 bar, a pressure downstream the reactor of 20 bar would be suitable. Excess gas is preferably separated from the formed hydrate particles in one or more cyclones, or similar apparatus for the separation of solid matter from a fluidum, whereupon the hydrate optionally is transferred to a suitable apparatus 12 for agglomerating the particles, e.g. by drum treatment and stirring, pressing, extruding, heat treatment and drying, or liquid suspension, of which drum treatment, pressing and extruding are the preferred methods, as described in further detail below.

Before the water is supplied to the reactor, it can be ventilated to remove oxygen and other gases (not shown). The water can be treated with stabilizing agents, additives and/or supplied with small seeds of hydrate crystals (as stated above). The stabilizing agents increase the storage and transportation ability of the hydrate particles with embedded gas. These agents may be produced on the spot from hydrocarbon fractions separated from the starting material, either from natural gas or natural gas together with other hydrocarbons. The additives can be compounds that decrease the surface tension of water, thus increasing the reaction rate for the formation of gas hydrate.

As set forth above, the hydrate forming reaction is exothermic, but the contribution from expansion of gas by utilizing the Joule-Thomson effect to the total cooling requirement is small. For example, the heat of formation for natural gas hydrate from the composition stated in FIG. 1 at temperatures above ca. 0° C. is about 2075 kJ/kg. Accordingly, the hydrate reactor must be cooled, either directly or indirectly. Direct cooling can for example be provided by circulating excess gas through an external refrigeration plant. In such cases, a need for an additional compressor will arise. Indirect cooling 6A can be accomplished with a cooling jacket or cooling elements, e.g. provided with a coolant from a closed circuit cooling system in the form of a refrigeration unit.

The mass and energy balance of the stream supplied to the reactor vessel is preferably adjusted to convert the substantial part of the water to hydrate particles, thus operating the process with excess gas. The reactor vessel can also be operated with excess water, and then, water must be separated away. The process can also have gas and water in excess. However, operating the reactor with excess gas is preferred. In this way, dry hydrates are formed that will decrease the risk of accumulation of hydrate and blocking of the reactor outlet.

Minor amounts of gas and any water can flow along with the hydrate particles. The unreacted and removed components of gas and flowing water can be recirculated; water 7a is recirculated and combined with the fresh water feed 7, and separated gas 1c is compressed, cooled and passed directly back to the reactor. Compressing the recirculated gas to a pressure a little above the reactor pressure is sufficient so that the gas easily flow into the same. The recirculated streams can also be treated with additives and further treated with respect to production of hydrate particles (not shown). Unreacted gas from the reactor is optionally compressed and supplied to another similar system operated at a higher pressure.

The hydrate particles with emedded gas are transported, as described above, optionally to equipment agglomerating or collecting the small particles to larger particles. The first hydrate particles are cooled and/or refrigerated in a refrigeration unit 11 prior to entering the agglomeration step 12. Cooling and freezing can be accomplished by pressure change, direct supply of cooled/refrigerated gas and/or indirect heat exchange. The purpose of the agglomeration is to agglomerate the hydrate to decrease its volume and simultaneously provide volume for gas storage in the particle pore volume. The compression or "agglomeration" can occur at pressure and temperature conditions chosen to achieve an optimum gas content and particle stability, i.e. the pressure and temperature must be at the high pressure side/low temperature side of the equilibrium curve for hydrate formation (FIG. 1). Additives can be mixed with the hydrate particles to improve their properties. Depending on the process conditions chosen, the total mass percent of gas can in general be in the range from 10 to 40 percent of the particle weight. After the agglomeration, the hydrate particles 8b can be cooled and/or refrigerated, thus keeping the total gas content inside the particle. The diameter of the compressed hydrate particles varies with the method used for agglomeration and the degree of compression desired, but a typical particle diameter for agglomerated natural gas hydrate particles is for example 2–20 mm. Likewise, the density will vary with the agglomeration method and degree of agglomeration, but a typical density is e.g. in the range from 850 to 950 kg/m$^3$.

If desired, the agglomerated hydrate particles are transported to an apparatus 13 that covers the gas impregnated particles with a pure ice shell by spraying the particles with water that freezes and forms an ice shell on the particles. For example, this can be accomplished by spraying the agglomerated particles 8b with water 15 via nozzles 16 whereas the particles are transported downstream by means of a mass transporter 14, e.g. a conveyor. The hydrate particles covered by ice are then cooled in a cooling apparatus 17. The ice shell thickness may be varied as required, but in general it is sufficient that the ice shell has a thickness from 0.5 to 1.5 mm. This process step of covering the hydrate particles with ice can be accomplished in several steps to further stabilize the hydrate particles by recirculating the partly ice-covered hydrate particles in stream 8c back to the same operation 13, or transporting the same to a following step (not illustrated). Cooling in the cooling apparatus 17 can for example be accomplished with a cooled methane based mixture at a pressure and a temperature outside the conditions favouring the hydrate formation. The ice shell has two major effects on the stability of a hydrate particle. Firstly, diffusion of gas from inside the particle to the environment is prevented because diffusion of gas through ice is negligble. Secondly, the ice shell provides a protecting shell that withstands a higher internal pressure from the particle. It can be verified that a spherical ice shell (pure ice) having a diameter of 15 mm and a shell thickness of 1 mm is able to withstand an internal pressure of about 5 bar. This pressure is in theory sufficient to prevent a typical natural gas hydrate from decomposing at temperatures below −13° C. at atmospheric pressure. However, experiments carried out in connection with the present invention has revealed that hydrates are stable even at temperatures as high as −1.5° C., but the stability will of course increase with decreasing temperature. To improve this effect further, the ice shell is optionally provided with reinforcing materials, such as fibers. The ice strength increases with decreasing temperature and with the use of fiber reinforcement. The fiber material can also be supplied at the first particle production by addition to the pressurized and cooled water or in other ways, e.g. by adding hydrate particles to the fiber material followed by mixing in a mixing unit, prior to the water spraying step. Moreover, the fiber material is optionally added in the agglomeration step when producing larger hydrate particles from the smallest gas filled hydrate particles. The produced, agglomerated and cooled hydrate particles 8d, optionally provided with ice shell, are then ready for transportation or storage.

Figure 4:
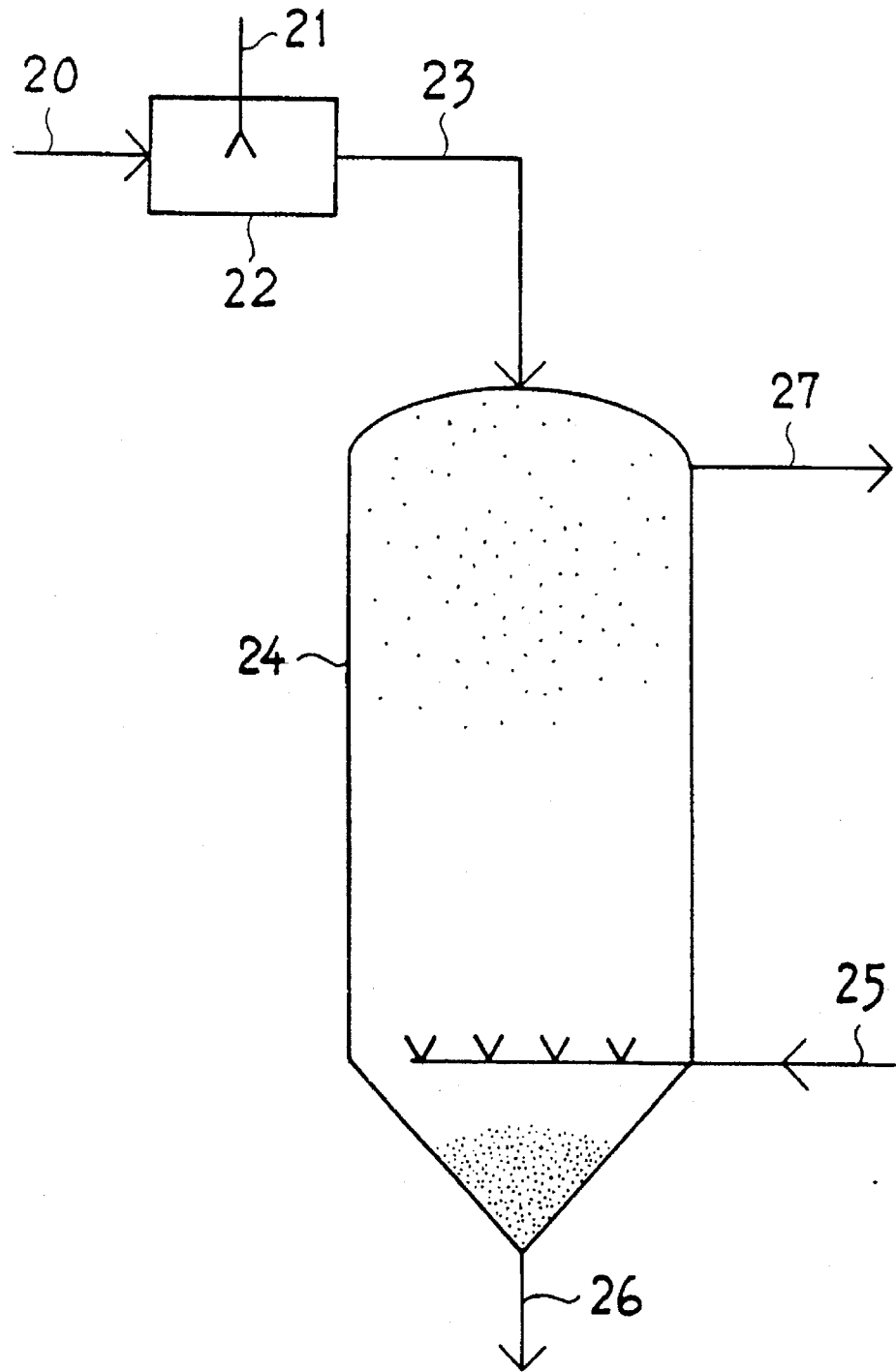
FIG. 4 illustrates an alternative method for providing a protecting ice shell on hydrate particles.

An alternative mode of providing an ice shell on the hydrate particles is illustrated in FIG. 4. In this method, the hydrate particles 20 formed are wetted by spraying with water 21 in, for example, a separate chamber 22. The wetted hydrate particles 23 are then guided into the top of a tower 24 and brought in direct contact with cooled gas 25 downstream that is supplied to the tower 24 at the bottom of same. The cooled gas, e.g. natural gas, cools the wetted hydrate particles to effect freezing of the water to establish a protecting ice shell on same, whereupon the hydrate particles covered by ice are removed from the tower in stream 26. This method provides for proper cooling of the wetted hydrate particles and results in a homogenous ice shell on the individual hydrate particles.

Such gas containing hydrate particles can be produced at offshore platforms or onshore. The platforms can be temporary or permanent. Onshore, the hydrate particles can be produced at a location close to hydrocarbon sources or other locations. The gas supplied in this way can be natural gas or natural gas together with other constituents. It can also be pollution gas to be transported away for further treatment.

EXAMPLE 1

This example illustrates one alternative method for the production of hydrate from natural gas by using the method of production in accordance with the invention, in which a relatively high reactor pressure of about 50 bar is applied.

Natural gas or associated gas is compressed and treated to remove components heavier than methane, ethane and propane in a manner known per se. The resulting mixture comprises 92% methane, 5% ethane and 3% propane (mole percent).

The treated gas mixture having the composition set forth above is then compressed to about 100 bar, supplied to a hydrate reactor through a nozzle and expanded to a pressure of about 50 bar. At the same time, water having a temperature of about 10° C. is compressed to about 100 bar and supplied to the reactor by expansion through separate nozzles, thus forming small droplets that disperses in the expanded gas phase. However, the Joule-Thomson cooling from the expansion of the gas from 100 to 50 bar constitutes only 43 kJ/kg, i.e. about 2% of the total cooling requirement, and the remaining cooling requirement is realized by using external cooling; cooling jacket and cooling elements supplied with recirculated liquidous propane coolant including cooled compressed recycle gas. The temperature and the pressure at the reactor inlet is 13° C. and about 50 bar, respectively, and according to the equilibrium curve for this composition (FIG. 1), this condition is located just inside the hydrate forming area.

The natural gas hydrate formed, having a snow like consistence, falls down toward the reactor bottom by the force of gravity and exits the reactor to an environmental pressure of about 10 bar. The individual hydrate particles then have a density of about 920 kg/m$^3$ and a gas content corresponding to 160–170 std. m$^3$ pure natural gas per m$^3$ hydrate powder, and comprise of about 15 mass percent natural gas and the remainder water. Typically, the particle size is from 1 to 10 mm. The hydrate powder is withdrawn from the reactor by the gauge pressure in the reactor, whereupon unreacted gas and water is separated from the gas hydrate formed, pressurized, cooled and transferred back to the reactor 6; the volume stream of the recirculated gas is about 10 times as great as the amount of fresh gas fed to the reactor. The hydrate is then cooled to −15° C. and compressed/agglomerated by pressing in a hydraulic press to a resulting particle size of about 5–15 mm, thus providing more embedded gas.

The produced agglomerated natural gas hydrate is then transported by means of cooled natural gas to storage vessels or to a transportation vessel. The cooled natural gas cools the natural gas hydrate by direct contact during transportation to a temperature of about −15° C., a temperature sufficiently low for this type of hydrate. The cooled natural gas hydrate is stored/transported in well insulated containers, preferably provided with a refrigeration unit, at a pressure close to atmosphere. The meta stable natural gas hydrate remains stable at these adiabatic storage conditions and withstands storage and transportation for several weeks without the need for converting back to pure natural gas.

EXAMPLE 2–4

These examples were provided to illustrate storage stability at different temperatures for the gas hydrates in accordance with the present invention.

EXAMPLE 2

Figure 5:
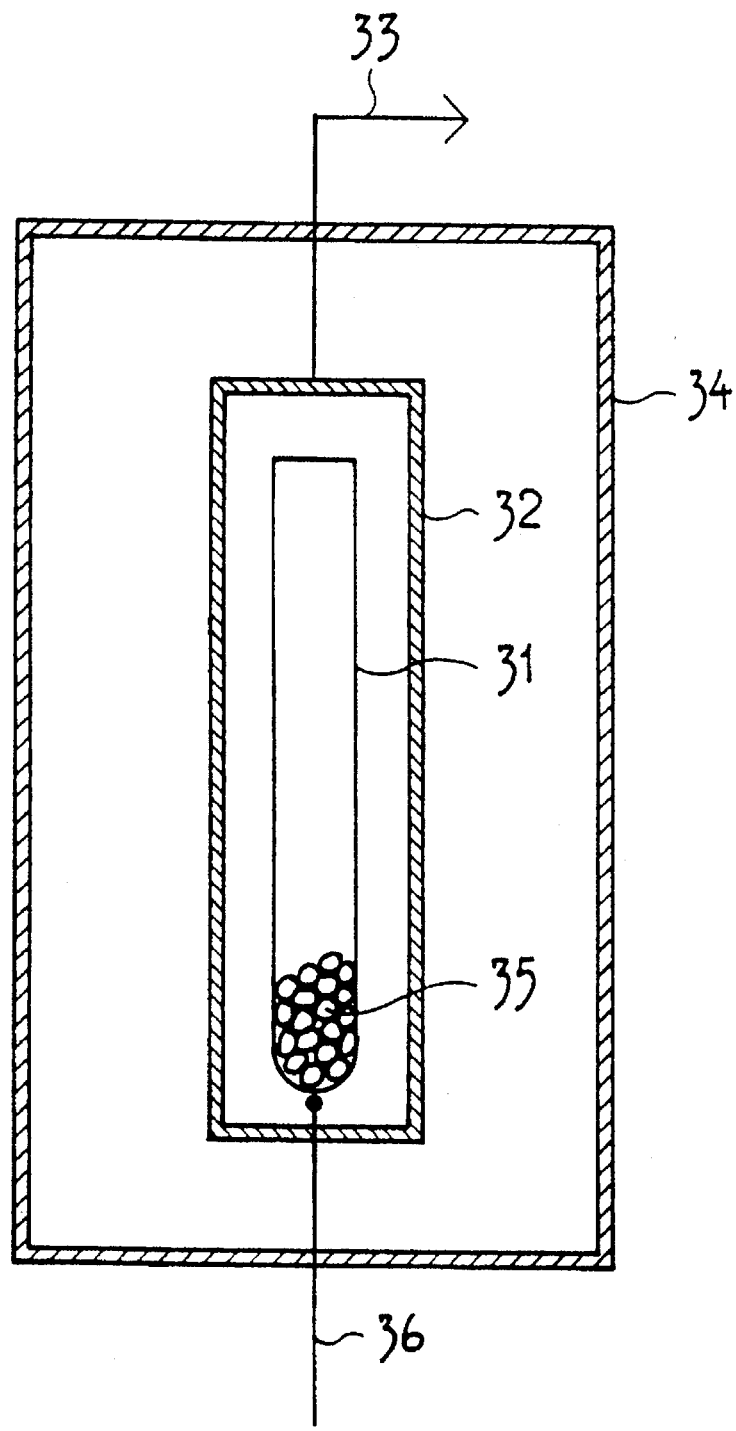
FIG. 5 illustrates schematically an experimental arrangement to measure the storage stability of gas hydrates.

Laboratory tests were carried out to test the thermal stability of a natural gas hydrate produced from the same natural gas composition as set forth in example 1. This natural gas hydrate was produced in a testing batch reactor at high pressure and moderate temperature. The hydrate was removed from the reactor and cooled to minus 5° C. in such manner that no decomposition occured; i.e. the natural gas hydrate did not decompose during transportation from the reactor to the equipment used for measuring the thermal stability. The equipment is illustrated in FIG. 5.

The solid hydrate 35 was located in a test tube 31 inside a closed container 32 and located in a container 34 at a constant temperature of minus 5° C. The closed cylinder 32 was kept at atmospheric pressure and connected with equipment for volumetric registration of any natural gas evolved/emitted from the gas hydrate. The test tube 31, the closed cylinder 32 and the external container 34 at constant temperature were constructed to maintain almost adiabatic conditions in the test tube; i.e. heat was neither removed from nor added to the test tube. To the bottom of the test tube 31 a temperature gauge 36 was attached to measure the temperature in the gas hydrate.

The solid hydrate was stored in the test tube at minus 5° C. for a long period of time. The solid hydrate was stable and gave no indication of decomposing to gas and ice; i.e. no gas emission from the test tube was measured.

EXAMPLE 3

The test tube 31 from example 2 above including the solid hydrate 35 and the closed container 32 was moved to another container 34 having a constant temperature. This second container 34 had a temperature of +5° C. The closed container 32 and the test tube were gradually heated, and the solid hydrate started to decompose to gas and liquid water.

Figure 6:
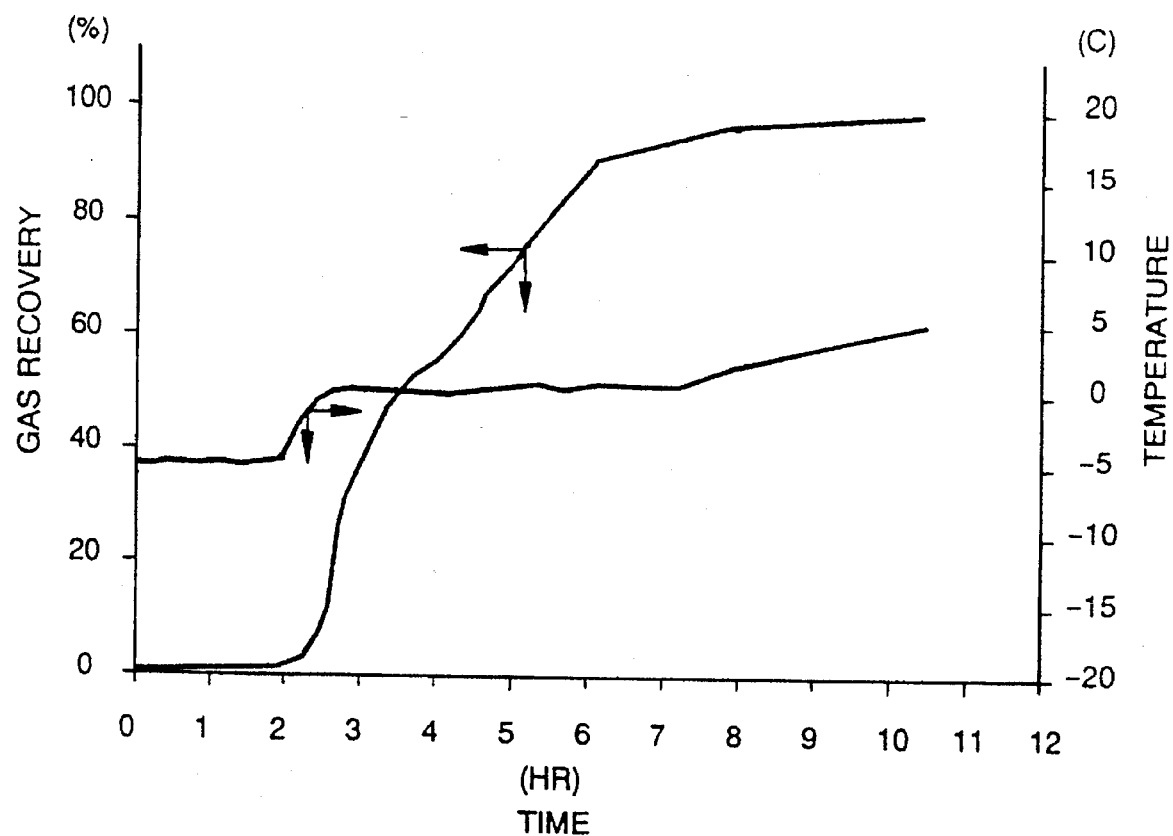
FIGS. 6 and 7 show temperature change and amount of gas emitted as a function of time during the testing of storage stability of natural gas hydrate in accordance with the experimental arrangement in FIG. 5.

The results from these experiments are illustrated in FIG. 6. The vertical axis to the left shows the percentage of gas emitted during the heating process. The last two hours of the storage period at near adiabatic conditions is illustrated in the figure; i.e. a storage temperature of minus 5° C. and no emission of natural gas. When the test tube and the surrounding cylinder were removed from minus 5° C. to plus 5°, the temperature in the test tube started to increase, whereupon the natural gas hydrate started to decompose. The test tube temperature is shown in FIG. 6 and is an approach to the real temperature in the solid natural gas hydrate, as appears from the construction of the testing apparatus in FIG. 5. All gas was removed within 6 hours (from 2 to 8 hours in FIG. 6). The approached temperature in the test tube increased relatively fast (during about 0.5 hours) from minus 5° C. to about 0° C. The temperature was constant at about 0° C., whereupon the natural gas hydrate decomposed (melted), as shown by the amount of natural gas evolved. When all natural gas was melted, the test tube temperature increased to about +5° C., the same temperature as in the surrounding container 34.

EXAMPLE 4

Figure 7:
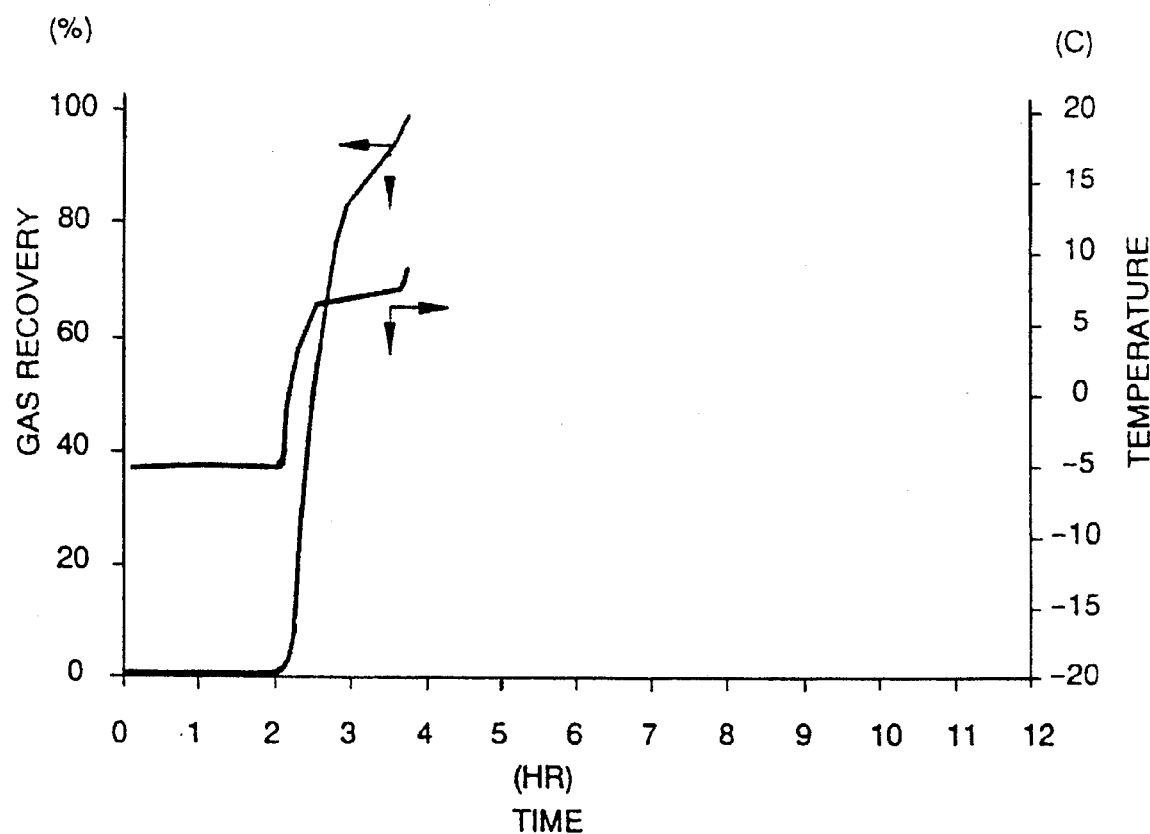

Another experiment was carried out by using the natural gas hydrate 35 produced and treated in the same manner as in Example 2, and the same storage temperature was used (−5° C.). After having stored the solid hydrate 35 at this temperature for a longer period of time without observing any emission of natural gas from the hydrate, the test tube 31 and the surrounding cylinder 32 were moved to a third container 34 having a constant temperature of about +20° C. The results of this experiment is shown in FIG. 7. When the test tube 31 and the surrounding cylinder 32 were moved to a higher temperature (here indicated as 2 hours), the temperature in the test tube 31/35 started to increase, and the solid hydrate 35 started to decompose (melt). About 2 hours later (shown as 4 hours in FIG. 7), all natural gas had escaped. During this period of time the test tube temperature increased rapidly to about +5° C. When the solid hydrate was melted, the test tube temperature increased to about +20° C. (not shown).

As appears from FIGS. 6 and 7, a natural gas hydrate can be heated at different rates, and the duration of the heating period affects the rate of decomposition; i.e. the rate for gas recovery, e.g. when unloading hydrate from a tanker to a terminal onshore. The amount of gas recovered will be the same for different heating rates.

Other similar experiments have been carried out in connection with the present invention. They show that a typical natural gas hydrate can be stored in a stable state at a temperature below the normal water freezing point; a test with a surrounding temperature of minus 1.5° C. resulted in stable hydrate at adiabatic conditions. A storage temperature of −5° C. was used in Examples 2–4 above. Other storage temperatures (freezing temperatures) are also applicable. The storage temperature chosen will depend on the application in question; i.e. what extent of hydrate stability is required. It should be understood that the stability of the solid hydrate that is stored may be dependent on the storage temperature; a lower storage temperature results in a more stable gas hydrate. A gas hydrate that is to be stored for a longer period of time should be stored at a lower temperature than a hydrate that is to be stored for only a short period of time.

What is claimed is:

1. A method for transportation or storage of a gas selected from the group consisting of natural gas, associated natural gas, methane, ethane, propane, carbon dioxide, combinations thereof with hydrogen sulfide and mixtures thereof by conversion to a gas hydrate, comprising the steps of:
    a) supplying a gas to a reactor maintained at a temperature and pressure sufficient for formation of a hydrate of the gas, and simultaneously supplying to the reactor water in the form of droplets which disperse in the gas, the gas and water droplets reacting to form particles of the gas hydrate;
    b) withdrawing the hydrate from the reactor, removing any unreacted gas or water therefrom, and recirculating any unreacted gas or water back to the reactor;
    c) agglomerating the particles of gas hydrate to increase particle weight and to embed further gas in interstices between particles of gas hydrate; and
    d) transporting or storing said agglomerated gas hydrate particles at a pressure of about atmospheric pressure under substantially adiabatic conditions obtained by insulation, refrigeration or insulation and refrigeration sufficient to maintain said particles at a temperature of about 0° to −15° C., said agglomerated gas hydrate particles being in metastable form at said pressure and said temperature.

2. Method in accordance with claim 1, comprising supplying said water to the reactor through at least one nozzle.

3. Method in accordance with claim 2, wherein said gas and water are supplied to the reactor through the same nozzle.

4. Method in accordance with claim 1, additionally comprising providing the agglomerated hydrate particles with a protective ice shell in at least one separate treatment step to improve fracture strength of the hydrate particles by spraying the particles with water that freezes to an ice shell on the hydrate particles and cooling the ice covered hydrate particles.

5. Method in accordance with claim 4, wherein the hydrate particles are provided with an ice shell by wetting them with water and bringing in direct countercurrent contact with upward rising cooled gas, thereby freezing the water to a protecting ice shell.

6. Method in accordance with claim 5, wherein the hydrate particles, the ice shell or both particles and shell are strengthened with a reinforcing material, supplied to the hydrate particles via the water that forms the shell.

7. Method in accordance with claim 1, comprising treating water with a stabilizing agents, prior to the supply of the water into the vessel.

8. Method in accordance with claim 1, wherein pressure and temperature of the gas prior to the supply to the reactor and pressure and temperature in the reactor are adjusted to provide a cooling of the gas by expansion into the reactor.

9. Method in accordance with claim 1, wherein the agglomeration of gas hydrate is carried out by drum treatment and agitation, pressing, extruding, heat treatment and drying, or suspending in a liquid.

10. Method in accordance with claim 1, additionally comprising cooling the particles of gas hydrate after said removing and before said agglomerating.

11. Method in accordance with claim 1, wherein said temperature is about −10° to −15° C.

12. Method in accordance with claim 1, wherein said gas is selected from the group consisting of methane, ethane, propane and mixtures thereof.

13. Method in accordance with claim 1, wherein said gas is supplied from natural gas, natural gas mixed with other hydrocarbons or water, pollution gas, or gas to be supplied to an industrial or biotechnical process.

14. Method in accordance with claim 1, wherein said gas additionally comprises water.

15. Method in accordance with claim 6, wherein said reinforcing material comprises fibers.

16. Method in accordance with claim 7, wherein said stabilizing agent is selected from the group consisting of separated hydrocarbon fractions and small hydrate crystal seeds.

17. Method in accordance with claim 8, wherein the reactor is cooled to a temperature from 1° to 10° C. below an equilibrium temperature at which said gas hydrate is produced.

18. Method in accordance with claim 11, wherein said agglomeration is carried out by drum treatment, pressing and extruding.

19. In a process comprising conversion of a gas to a gas hydrate and transporting or storing the gas selected from the group consisting of natural gas, associated natural gas, methane, ethane, propane, carbon dioxide, combinations thereof with hydrogen sulfide and mixtures thereof in gas hydrate form, the improvement comprising transporting or storing the gas hydrate at a pressure of about atmospheric pressure under substantially adiabatic conditions obtained by insulation, refrigeration or insulation and refrigeration sufficient to maintain said particles at a temperature of about 0° to −15° C., said gas hydrate being in metastable form at said pressure and said temperature.

20. Method in accordance with claim 19, wherein said transporting or storing is carried out in an insulated container.

* * * * *